United States Patent [19]

Hauser et al.

[11] Patent Number: 4,541,728
[45] Date of Patent: Sep. 17, 1985

[54] DEVICE AND METHOD FOR MEASURING HEAT FLUX AND METHOD FOR FORMING SUCH A DEVICE

[75] Inventors: Ray L. Hauser, 5758 Rustic Knolls Dr., Boulder, Colo. 80301; Rodney B. McKeever, Boulder, Colo.

[73] Assignee: Ray L. Hauser, Boulder, Colo.

[21] Appl. No.: 517,202

[22] Filed: Jul. 25, 1983

[51] Int. Cl.[4] .............................................. G01K 17/00
[52] U.S. Cl. .......................................... 374/29; 374/30
[58] Field of Search ....................... 374/29, 30, 31, 32; 136/241, 226

[56] References Cited

U.S. PATENT DOCUMENTS

| 1,528,383 | 3/1925 | Schmidt | 374/30 |
| 3,238,775 | 3/1966 | Watts | 374/30 |
| 3,382,108 | 5/1968 | Wilkins | 136/226 |

Primary Examiner—Charles Frankfort
Assistant Examiner—David R. Schuster
Attorney, Agent, or Firm—O'Rourke & Harris

[57] ABSTRACT

A device and method are disclosed for measuring heat flux, as is a method for forming a device for such use. Thermopile junctions are formed on a belt-like support so that the heat flux from an article, such as a pipe or process equipment, is sensed while the support is positioned against a surface of the article, and a voltage indicative of the sensed heat flux is generated and coupled to an outlet connector adapted for connection to a voltage readout device. The belt-like support is relatively narrow, flexible, and has one side of a polymer with high infrared emissivity and the other side of a metal foil with low infrared emissivity. The support has mounted thereon a pair of thermopile elements each of which includes a non-metallic core having a high electrical resistance wire wound thereon, with a like portion of each turn of wire wound on the core having a low electrical resistance metallic plating thereon whereby heat flux through each thermopile element causes a temperature differential at opposite sides of the core which generates a thermoelectric current to thus provide a DC voltage that is coupled on the wound wire to an output connector at one end of the belt-like support. A second connector at the other end of the belt-like support has a bridging connector connected thereto during use for connecting the wound wires of a pair of thermopile elements, and the effective length of the device can be increased by connecting together a plurality of supports having thermopile elements mounted thereon through the connectors.

21 Claims, 4 Drawing Figures

U.S. Patent    Sep. 17, 1985    4,541,728
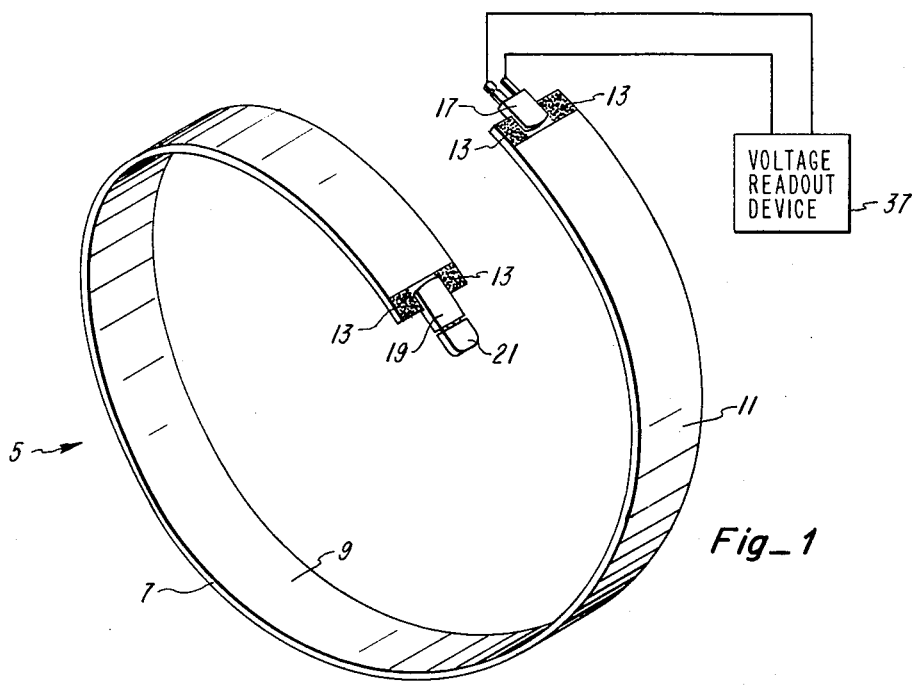
Fig_1
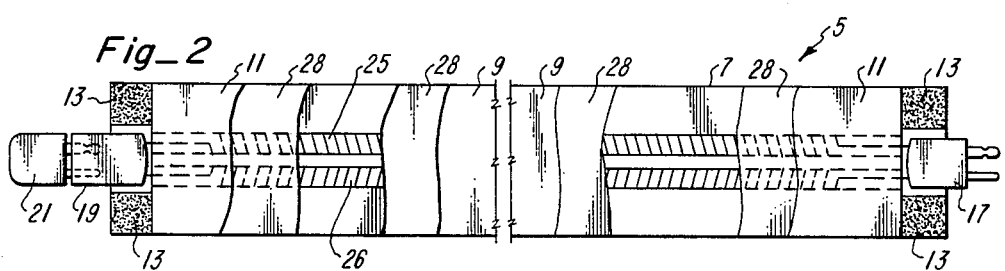
Fig_2
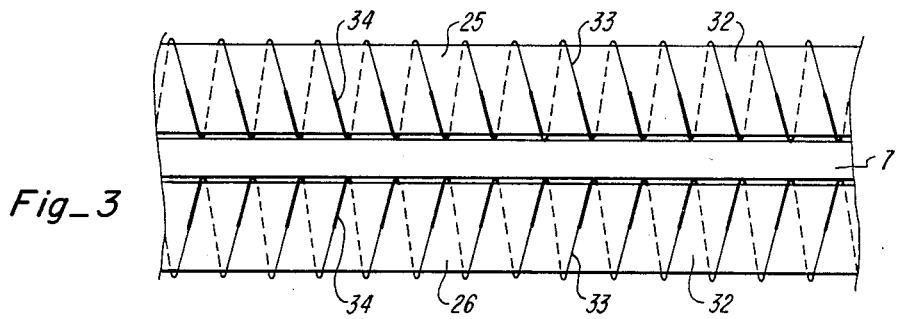
Fig_3
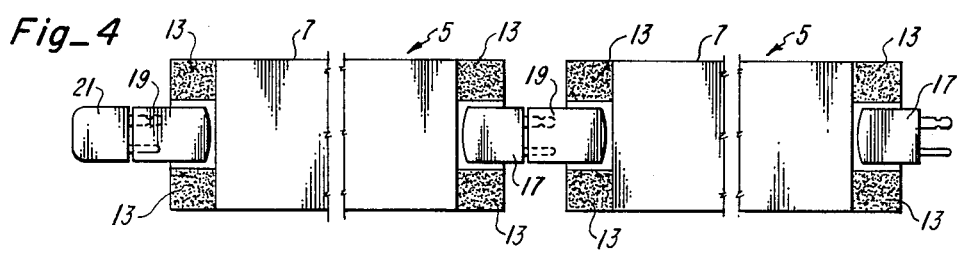
Fig_4

DEVICE AND METHOD FOR MEASURING HEAT FLUX AND METHOD FOR FORMING SUCH A DEVICE

FIELD OF THE INVENTION

This invention relates to a device and method for measuring heat flux, and, more particularly, relates to a flexible belt-like device for measuring the heat flux of an article, such as a pipe or process equipment, a method for measuring the heat flux of such an articles, and a method for making such a device.

BACKGROUND OF THE INVENTION

It is oftentimes necessary and/or desirable to be able to quickly and accurately measure the heat flux of an article such as a pipe or process equipment.

While devices and/or methods have heretofore been suggested for measuring heat flux in general, a relatively simple device that can be quickly positioned and yet provide an accurate reading has not been heretofore available.

SUMMARY OF THE INVENTION

This invention provides a device and method for quickly and accurately measuring the heat flux of an article and for forming a device for measuring such heat flux. The heat flux of an article is sensed by a thermopile element and a voltage generated that is indicative of sensed heat flux. A flexible belt-like support has the thermopile element mounted thereon with the support being adapted to engage a surface of an article to be tested.

It is therefore an object of this invention to provide an improved device and method for measuring heat flux.

It is another object of this invention to provide an improved device and method for measuring the heat flux of an article that is relatively simple both in construction and utilization and yet provides an accurate indication of heat flux of the article tested.

It is still another object of this invention to provide an improved device and method for measuring heat flux that utilizes a thermopile element to sense heat flux.

It is still another object of this invention to provide an improved device for measuring heat flux utilizing a belt-like support having the heat flux sensing means substantially entirely mounted therein.

It is yet another object of this invention to provide an improved device for measuring heat flux that utilizes a thermopile element made up of high resistance wire wound on a non-metallic core with like portions of each turn of wire having low resistance plating material thereon.

It is still another object of this invention to provide an improved method for forming a device useful for measuring heat flux.

With these and other objects in view, which will become apparent to one skilled in the art as the description proceeds, this invention resides in the novel construction, combination, arrangement of parts and method substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a perspective view of the device of this invention;

FIG. 2 is a cut-away partial top view of the device shown in FIG. 1 illustrating the thermopile elements and connection of such elements with electrical connectors;

FIG. 3 is a partial cut-away top view of the device shown in FIGS. 1 and 2 illustrating the thermopile elements in more detail; and FIG. 4 is a partial view illustrating attachment of different sections of the device as shown in FIG. 1 to increase the effective length of the device.

DESCRIPTION OF THE INVENTION

Belt-like device 5 (hereinafter sometimes referred to as the belt) of this invention is shown in perspective form in FIG. 1. As shown, device, or belt, 5 includes a length of belt-like support material 7 having one side preferably of a high infrared emissivity polymer 9 and the other side preferably of a low infrared emissivity metal foil 11. When the belt is used, for example, to measure heat flux from a pipe having a bright aluminum jacket, the jacket emissivity can be matched by having a bright aluminum foil at the exposed side of the belt. Likewise, if the belt is to be used, for example, to measure energy loss from an apparatus having a painted, fabric or plastic jacket, the external side should be of high infrared emissivity for jacket emissivity matching purposes.

Mechanical anchoring means, such as Velcro strips, or tabs, 13, as shown in FIG. 1, are attached at each end of the length of material 7. Because even a small air gap between test surfaces can cause significant error in heat flux measurements, the belt is preferably pulled tightly against the test surface by using the Velcro strips in conjunction with a Velcro tape (not shown). A tight helical wrap is preferred to having an overlap of the ends of belt 5 that might disturb the equilibrium heat flux through the test surface. It has been found that a substantially complete wrap of belt 5 about a pipe, for example, provides an integrated measure of the heat flux which is usually different on the top, sides and bottom of a horizontal pipe.

A polarized male connector, or plug, 17 is located at one end of belt 5 and a polarized female connector, or plug, 19 is located at the opposite end of belt 5. As shown in FIG. 1, a polarized bridge connector 21 is utilized to connect the leads connected with female connector 19 when the device is in use.

As shown in FIG. 2, thermopile elements 25 and 26 extend substantially along the entire length of support material 7 and are preferably in engagement with adhesive 28 (which may be on one side of flexible tape 9 which has aluminum foil 11 on the other side). Each of these elements is electrically connected at opposite ends to male and female connectors 17 and 19 as brought out more fully hereinafter.

Support material 7 is used to provide spacing between the two thermopile elements 25 and 26 and as outer edges which have the function of guarding the elements to provide linear heat flux.

Thermopile elements 25 and 26 are shown in greater detail in FIG. 3. As shown, each element includes a flexible core 32, which core is preferably a long, narrow non-metallic section, such as, for example, a glass fabric covered with silicone elastomer. An electrical wire 33 having high electrical resistance is wound about the core in a continuous helical winding. Wire 33 is preferably a fine constantan wire.

A portion of each turn of wire 33 has a metallic plating 34 (preferably silver) plated thereon with the metallic plating having low electrical resistance and high thermoelectric potential relative to wire 33. The plating is preferably accomplished after the wire is wound on the core with the plating being applied to one edge and up to about one-half of each turn of the wound wire, as also indicated in FIG. 3. The pigtails of wire 33 (which are connected with connectors 17 and 19) are also preferably plated (again preferably with silver) to obtain low electrical resistance.

Multiple wraps of wire on core 32 have been found to provide an effective thermopile element. When such a thermopile element is placed on a warm surface, the heat flux through the element causes a temperature differential with one side being warmer than the other so that alternate thermopile junctions are warmer and cooler. This causes a thermoelectric current to be generated to produce a DC voltage.

As shown in FIGS. 2 and 3, thermopile elements 25 and 26 are positioned within belt 5 in spaced, parallel relationship with respect to one another. While not specifically shown, conventional spacing materials and flexible facings may be utilized as needed to maintain the desired positioning of the elements. As also shown in FIGS. 2 and 3, platings 34 are arranged about an axis of symmetry, thus providing a summation of DC voltages when an electrical connection is provided to connect the electrical junctions at connector 19 and a readout device, such as a voltmeter, 37, is connected with the electrical junctions of connector 17.

As indicated in FIG. 4, by use of male and female connectors 17 and 19 at the opposite ends of each belt 5, lengthwise expansion of the overall belt utilized to provide for testing of articles of different sizes can be achieved. For example, while a single belt 5 having a length of forty inches can be wrapped about a pipe that is twelve inches in diameter, it cannot be wrapped about a pipe that is twenty-four inches in diameter. However, by removing bridge connector 21 from female connector 19 and plugging a second section of belt 5 in series with the first section by connecting the male connector 17 of the second section to the female connector 19 of the first section (and then connecting the bridge connector 21 with the female connector 19 of the second section) an effective length of eighty inches is achieved which can be utilized for wrapping about a pipe having a diameter of twenty-four inches. Additional belts can be added as necessary and/or desired (however, a new calibration factor is used for combined belts).

For a working embodiment of this invention, a heat flux transducer was made by wrapping two sections of glass fabric coated with silicone elastomer to form two cores, with each core having dimensions of 1/16 inch in thickness, ¼ inch in width, and 40 inches in length. Fine constantan wire was then wrapped for approximately 1000 turns on each glass-silicone core.

An arrangement of each wire wound core was made so that edges of the constantan wrappings could be dipped only ⅛ inch deep in a silver-plating bath, using the constantan as a cathode. After the silver had been electroplated onto the constantan, each wire plated core was removed from the plating bath, washed, rinsed and then placed near the center of a tape two inches wide having pressure-sensitive adhesive on one side and aluminum foil on the other side. The two cores with the plated wire wound thereon were placed parallel with respect to one another with about ⅛ inch spacing therebetween, and outer edgings, made of ⅜ inch wide glass-silicone fabric, was similarly placed on the adhesive tape. The silver-plated portions of the turns of wire wound on each core were placed toward the center of the belt.

The silver-plated constantan pigtails were connected to the polarized connectors (preferably of copper as commonly used for thermocouples), and prepared tapes of Velcro hook material were attached to the end portions, after which the assemblies were covered with a silicone elastomer 1/32 inch thick by 2 inches wide and 40 inches long. Silicone elastomer adhesives were used to assist in assembly where needed. The final belt was ⅛ inch in thickness, 2 inches in width, and 40 inches in length.

The assembled belt was placed on a warm surface having a precalibrated rigid heat flux transducer, and the calibration coefficient was measured to be in the range of one millivolt per BTU/hour square foot heat flux. The final belt was sufficiently flexible for wrapping a helical pattern around pipes ranging upwards from 3 inches diameter.

In use, the belt is placed against a test surface of an article, such as an insulated pipe line or refrigerated line, to sense the heat flux. With the belt held tightly against the test surface, the energy flow (to or from the test surface) flows through the belt with little heat flow resistance caused by the belt. The temperature difference within the belt is sensed by the thermocouples on each side of the core portion of the belt, and the generated electrical voltage from these thermocouples is coupled from the belt to an externally connected voltage readout device. The heat flux through the belt is proportional to the measured voltage, and calibration of the device readily provides this mathematical relationship.

In view of the foregoing, it can be appreciated that this invention provides an improved device and method for measuring heat flux, as well as an improved method for forming a device for measurement of heat flux.

What is claimed is:

1. A device for measuring heat flux, said device comprising:

sensing means for sensing heat flux of an article to be tested, said sensing means including first and second thermopile elements each of which includes a plurality of thermopile junctions between which temperature differentials are sensed at predetermined spaced points when said sensing means is closely adjacent to a surface of said article, and each of said thermopile elements, responsive to sensed heat flux, providing an output voltage indicative thereof with said output voltages from said first and second thermopile elements being summed to provide a summation output voltage from said sensing means;

belt-like support means including flexible cover means for substantially entirely encasing said sensing means with said sensing means being located at the center one-third portion of the width of said belt-like support means and extending for substantially the entire length of said belt-like support means, and with said flexible cover means including a polymer at one side of said sensing means providing high infrared emissivity and a metal foil at the other side of said sensing means providing low infrared emissivity, said support means being adapted to maintain said sensing means closely adjacent to said surface of said article; and output means electrically connected with said sensing means, said output means being adapted to couple said summation output voltage indicative of said sensed heat flux from said device.

2. The device of claim 1 wherein said support means includes an adhesive layer within said cover means and having said sensing means releasably secured thereto.

3. The device of claim 2 wherein said support means also includes a layer of a silicone elastomer covering at least said sensing means.

4. The device of claim 1 wherein said support means has mechanical anchoring means at the opposite ends of said support means.

5. The device of claim 4 wherein said mechanical support means are Velcro strips.

6. The device of claim 1 wherein said belt-like support means is about $\frac{1}{8}$ inch in thickness, 2 inches in width, and 40 inches in length.

7. The device of claim 1 wherein said first and second thermopile elements include a core of electrically nonconductive material, a wire of high electrical resistance wound on said core, and plating material of low electrical resistance relative to said wire plated on predetermined portions of said wire.

8. The device of claim 7 wherein said wire is fine constantan wire, and wherein said plating material is silver.

9. The device of claim 7 wherein said plating material covers not more than one-half of each turn of said wire.

10. The device of claim 9 wherein said wire is helically wound on said core, and wherein said plating material is along one edge of said core so that each said plating material on each said partial turn of said wire is oriented parallel with respect to plating materials on adjacent said partial turns of said wire.

11. A device for measuring heat flux, said device comprising:

a pair of thermopile elements, each of said thermopile elements incuding a core of electrically nonconductive material, a wire of high electrical resistance wound on said core, and plating material of low electrical resistance relative to said wire plated on predetermined portions of said wire, each of said thermopile elements providing an output voltage indicative of the heat flux of an article when said thermopile element is closely adjacent to a surface of said article;

flexible belt-like support means having said pair of thermopile elements mounted thereon so that said elements are positioned with said plating material of each said element adjacent to but spaced from one another, said support means having a polymer at one side providing high infrared emissivity and a metal foil at the other side providing low infrared emissivity; and first and second connector means positioned at opposite ends of said support means, said first and second connector means each having a first electrical junction connected to different ones of the opposite ends of said wire wound on said core of one of said thermopile elements and a second electrical junction connected to different ones of the opposite ends of said wire wound on said core of the other of said thermopile elements whereby when said first and second electrical junctions of said first connector are electrically connected together a summation of said output voltage produced by said pair of thermopile elements is provided at said second connector that is indicative of said sensed heat flux of said article.

12. The device of claim 11 wherein one of said connectors is a polarized female connector and the other of said connectors is a polarized male connector, said device also including a bridging connector for connecting said first and second electrical junctions of said first connector.

13. The device of claim 11 wherein said device includes a second pair of thermopile elements mounted on a second flexible belt-like support means and having third and fourth connectors connected with said second pair of thermopile elements, said second pair of thermopile elements, said flexible belt-like support, and said third and fourth connectors being substantially identical to said first pair of thermopile elements, said first flexible belt-like support and said first and second connectors whereby the effective length of said device can be increased by connecting said first connector with said third connector and connecting together the electrical junctions of said fourth connector.

14. The device of claim 11 wherein said device includes a voltage readout means connected with said second connector to provide an output reading indicative of the sensed heat flux of said article tested.

15. A method for measuring heat flux, said method comprising:

providing a belt-like structure having a heat flux sensing means provided by a pair of thermopile elements substantially entirely mounted thereon;

positioning said belt-like structure tightly against a surface of an article to be tested to generate an output voltage at each thermopile element indicative of sensed heat flux and summing said output voltage from said thermopile elements to provide said output voltage that is indicative of the heat flux of said article sensed by said sensing means, said provided belt-like structure including flexible cover means for substantially entirely encasing said sensing means with said sensing means being located at the center one-third portion of the width of said belt-like support means and extending for substantially the entire length of said belt-like support means, and with said flexible cover means including a polymer of one side of said sensing means providing high infrared emissivity and a metal coil at the other side of said sensing means providing low infrared emissivity; and using said output voltage to provide an indication of the heat flux of said article.

16. The method of claim 15 wherein said method includes pulling said belt-like structure tightly against the surface of said article to be tested by means of Velcro strips with no overlapping of said belt-like structure.

17. The method of claim 15 wherein said method includes providing said pair of thermopile elements by providing an elongated narrow core of electrically nonconductive material, winding a wire of high electrical resistance on said core, and plating a predetermined portion of said wire with a plating material of a low electrical resistance relative to said wire.

18. The method of claim 15 wherein said method includes providing a voltage readout means, and calibrating said voltage readout by a known heat flux.

19. The method of claim 17 wherein said method includes dipping one edge of said core with said wire wound thereon in a plating bath to provide said plating on only said portion of said turn of wire on said core.

20. The method of claim 19 wherein said method includes providing constantan wire and winding said constantan wire on said core, and providing a silver plating bath into which said edge of said core is dipped to thereby plate silver onto said constantan wire.

21. The method of claim 17 wherein said method includes encasing said core and said core with said plated wire thereon in a silicone elastomer.

* * * * *